United States Patent [19]
Hui-Shieh et al.

[11] Patent Number: 5,961,801
[45] Date of Patent: Oct. 5, 1999

[54] DNA SEPARATION ELECTROPHORESIS GELS AND METHODS FOR THEIR USE

[75] Inventors: Chia Hui-Shieh, State College, Pa.; Azita Hedayati, Riverside, Calif.

[73] Assignee: Beckman Instruments, Inc., Fullerton, Calif.

[21] Appl. No.: 08/976,891

[22] Filed: Nov. 24, 1997

[51] Int. Cl.$^6$ .......................... G01N 27/26; G01N 27/447
[52] U.S. Cl. .......................... 204/469; 204/405; 204/456; 204/605; 204/606
[58] Field of Search ........................ 204/606, 607, 204/608, 609, 610, 612, 613, 614, 615, 616, 617, 618, 619, 620, 621, 468, 456, 457, 458, 459, 461, 462, 463, 464, 465, 466, 467, 469, 47 D, 605, 455

[56] References Cited

U.S. PATENT DOCUMENTS

| | | | |
|---|---|---|---|
| 3,047,489 | 7/1962 | Raymond | 204/616 |
| 4,732,930 | 3/1988 | Tanaka et al. | 524/742 |
| 4,865,706 | 9/1989 | Karger et al. | 204/605 X |

OTHER PUBLICATIONS

Hackh's Chemical Dictionary, 4th ed, edited by Julius Grant (1969) no month available p. 218.

Robin Martin "Gel Electrophoresis: Nucleic Acids" (1996) no month available pp. 27–28.

T. Nishikawa et al., Separation of long DNA fragments by capillary gel electrophoresis with laser induced fluorescence detection, *Electrophoresis,* no month available 1994, 15, 215–220.

W. Hou et al., DNA Sequencing with a Hexamer String Primer and Dye–Labeled Terminators, *Analytical Biochemistry,* 221, 136–141 no month available (1994).

D. McGregor, Detection of DNA fragments separated by capillary electrophoresis based on their native fluorescnece inside a sheath glow, *Journal of Chromatography A,* 680 no month available (1994) 491–496.

*Primary Examiner*—William H. Beisner
*Assistant Examiner*—John S. Starsiak, Jr.
*Attorney, Agent, or Firm*—William H. May; P. R. Harder; Sheldon & Mak

[57] ABSTRACT

A novel electrophoresis separation medium comprises polyacrylamide and a dioxane. An electrophoresis separation system comprises a separation channel, the separation channel including the novel separation medium. In a method for electrophoretically separating analytes by introducing analytes into a separation channel, an electric field is applied across the separation channel and the analytes are allowed to electrokinetically migrate within the separation medium. The separation channel comprises the novel electrophoresis separation medium.

21 Claims, 1 Drawing Sheet

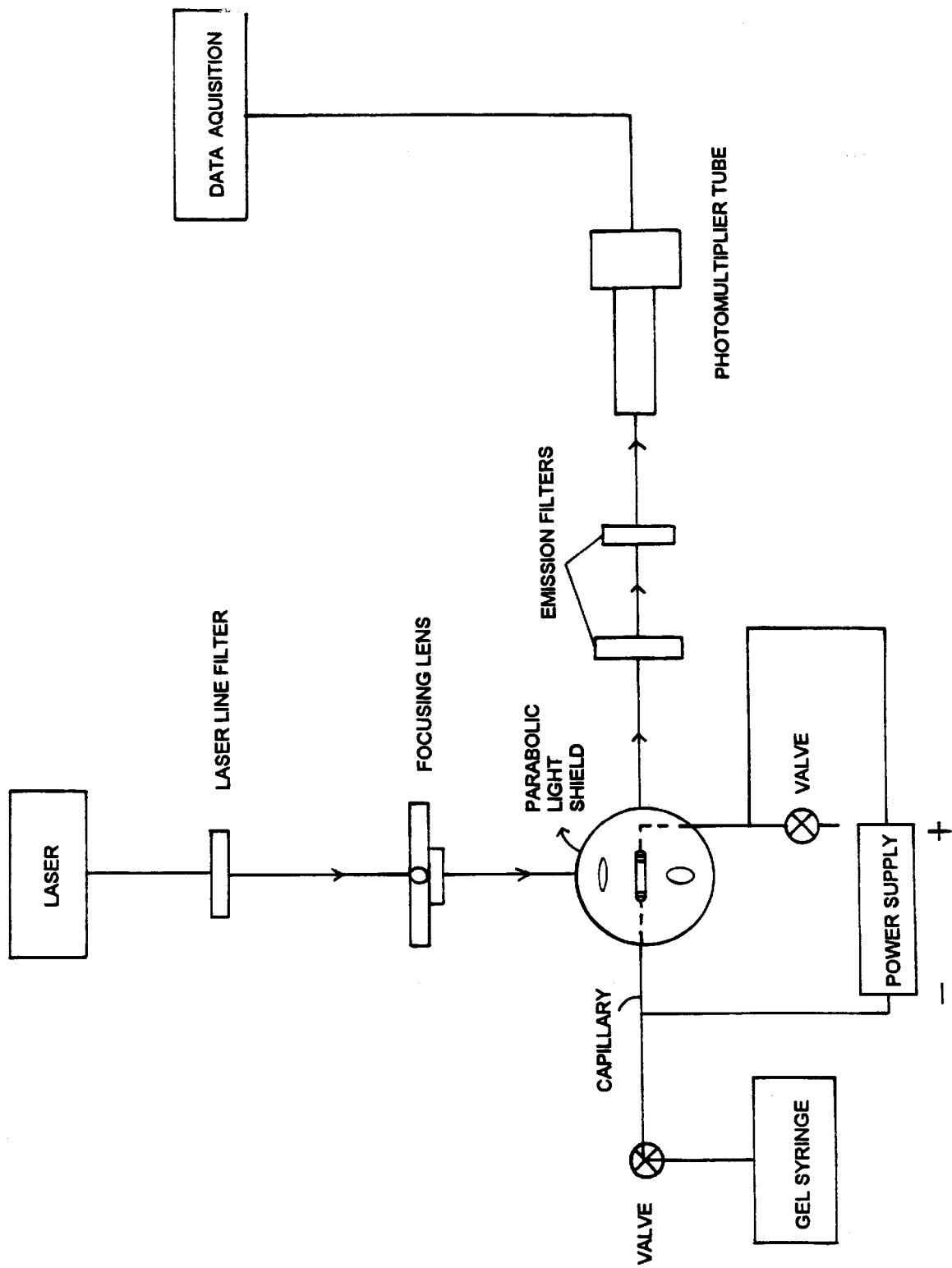

DNA SEPARATION ELECTROPHORESIS GELS AND METHODS FOR THEIR USE

BACKGROUND

The present invention generally relates to gels for separation mediums in electrophoretic systems. More particularly, the present invention involves improved separation medium gels and methods for their use in capillary electrophoresis based DNA separations.

For decades electrophoretic separation techniques have been the method of choice for separating charged molecules and in particular for separating proteins. Early electrophoresis applications and many current applications involve applying electric fields across separation medium gels which are prepared in the form of slabs of varying size and thickness. Samples loaded at one end of the slab migrate across the slab under the influence of the electric field. When the sample's charged components have different electrokinetic mobilities they migrate at different rates and physically separate as a result of their differing electrokinetic mobilities. Traditionally, slabs which vary in size from several inches on each side to several feet are fabricated of a separation gel. Typically these gels are crosslinked polyacrylamide or other water swellable gel systems such as agarose or cellulose.

In recent years capillary, electrophoresis (CE) techniques have become the electrophoretic separation method of choice for many biological researchers. Use of capillary electrophoresis for detection of DNA fragments is described by McGregor et al., "Detection of DNA Fragments Separated by Capillary Electrophoresis Based on Their Native Fluorescence Inside a Sheath Flow," *Journal of Chromatography A*, 680 (1984), 491–496; and Nishiwaka et al., "Separation of Long DNA Fragments by Capillary Gel Electrophoresis With Laser-Induced Fluorescence Detection," *Electrophoresis*, 1994, 15, 215–220. CE separations involve injecting samples into a buffer filled or gel filled capillary and generating the electric field across the capillary in order to cause sample components to electrophoretically migrate within the capillary. A variety of on-capillary column and off-capillary column detection techniques can be used to detect the components including uv, visible, fluorescence and electrochemical detection. CE offers many advantages over slab gel electrophoresis techniques. CE is available in fully automated systems which include automated injectors and data storage and analysis features and relatively easy to use detection systems. Additionally, CE separations are more rapid than slab gel separations and their separation mediums can be replaced after each analysis for a subsequent analytical run.

Electrophoresis applications have expanded to include a wide range of charged analytes and analytes which can be derivatized to incorporate at least one charge moiety in order to provide the analyte with an electrophoretic mobility. Thus, in addition to proteins, peptides, and amino acids, electrophoretic separation methods are useful for separating derivatized polysaccharides and oligosaccharides, glycoproteins, nucleic acids and oligonucleotides and charged compounds in general. Particularly noteworthy is the demand by The Human Genome project and other large scale DNA sequencing projects for the capability of separating and identifying large numbers of DNA fragments in a single analysis. Because of the huge number of bases which must be sequenced in these projects, the success of the projects largely depends upon the ability to automate and speed the sequencing process. Because electrophoresis is the primary analytical method used for DNA sequencing, rapid DNA sequencing requires electrophoresis techniques which are not only fast but can resolve many bases in a single analysis.

Slab gel electrophoretic methods using slabs fabricated of crosslinked acrylamide can separate and resolve over 600 bases in a single analytical run. A major disadvantage associated with the slab approach is that they require many hours to perform a single analysis.

Capillary electrophoresis, on the other hand can perform a single run and effectively separate up to about 400 bases in less than an hour. Thus, capillary electrophoresis systems incorporating multiple capillaries in a single automated system offer the advantage of being able to analyze multiple samples in less than an hour. The major limitation associated with capillary electrophoresis in DNA sequencing is the separation medium itself. Like slab gel electrophoresis, DNA sequencing samples traditionally have been analyzed using polyacrylamide separation mediums. In order to remove the gel medium from the capillary and replace it with fresh medium the DNA separation mediums used in capillaries preferably have flow characteristics which allow the medium to flow in and out of capillaries. Thus, unlike traditional slab gel separation mediums which typically use crosslinked polyacrylamide having high viscosity and extensive elasticity properties, capillary electrophoresis separation mediums typically include linear polymers or very lightly crosslinked polymer gels which are present at lower concentrations than slab gel separation mediums and which are capable of being pressure forced to flow in and out of capillaries. Many of these separation mediums are based upon polyacrylamide and include denaturants such as urea and/or formamide. The denaturants improve the DNA fragment separation resolution and DNA sequencing read length, but often result in problems connected with their precipitation from the medium. Moreover, urea containing gels have viscosities which are sufficiently high to cause problems in replaceable gel systems and gels incorporating formamide are not stable in aqueous mediums and thus are associated with short shelf lives.

While these denaturing containing polyacrylamide systems work reasonably well there is an ongoing need for separation mediums which provide longer read length and improved resolution. There is also an ongoing need to provide CE separation mediums which incorporate denaturants at sufficiently high concentration without their precipitation from the separation medium. There is further a need to provide CE separation mediums having extended shelf lives and sufficiently low viscosity to allow the separation mediums to easily flow into and out of capillaries.

It is accordingly an object of the present invention to provide separation mediums suitable for use in capillary electrophoresis systems having read lengths of up to over 500 bases. It is also an object of the present invention to provide separation mediums having suitable denaturants which will not precipitate from the medium system, having extended shelf lives and can be used in replaceable gel systems.

SUMMARY

This invention includes an electrophoresis gel separation medium comprising polyacrylamide and a dioxane.

The invention further includes a electrophoresis gel separation system comprising an elongated separation channel, said separation channel including a separation medium comprising polyacrylamide and a dioxane.

The invention still further includes the method for electrophoretically separating analytes by introducing analytes into a separation channel, applying an electric field across the separation channel and allowing the analytes to electrokinetically migrate within the separation medium, the improvement wherein the separation channel comprises an electrophoresis gel separation medium comprising polyacrylamide and a dioxane.

The present invention provides separation mediums and separation systems which when used in connection with electrophoresis separations result in improved analytical resolution and improved DNA sequencing read length. Advantageously, the separation mediums of the present invention include denaturing compounds which do not cause an increase in the separation medium viscosity and thus are suitable for use in replaceable gel electrophoresis systems. The decreased viscosities and improved flow properties associated with the separation mediums of the present invention provides means that the separation mediums can be forced in and out of capillaries using less pressure than prior art systems. Furthermore, the separation mediums of the present invention are stable in an aqueous environment making them suitable in applications in which the separation medium is for a length of time prior to its use.

The present invention is based upon the discovery that dioxane can be incorporated in polyacrylamide solutions to provide electrophoretic separation mediums having suitable biopolymer denaturing characteristics and highly improved DNA resolution and read length characteristics. Thus, in accordance with one aspect, the present invention provides separation mediums of polyacrylamide and dioxane. In preferred embodiments, the separation mediums incorporate one or more additional denaturants and further include one or more buffer compounds which typically acts as the electrophoresis electrolyte.

DRAWING

These and other features, aspects, and advantages of the present invention will become better understood from the following description, appended claims, and accompanying drawing where:

The FIGURE which schematically shows capillary electrophoresis system utilizing a gel separation medium according to the present invention.

DESCRIPTION

A gel according to this invention includes polyacrylamide and a dioxane in an effective resolution enhancing amount, preferably on the order of about 1 to about 5 grams polyacrylamide and about 5 to about 30 ml of a dioxane, per 100 ml of the gel.

In the most preferred embodiments, the gel includes about 3 grams polyacrylamide, about 15 ml dioxane (1,4 dioxane and/or 1,3 dioxane), about 3.5 M urea, and about 100 mM tris-borate buffer, with the balance being water, to make a total gel volume of 100 ml.

In accordance with another aspect of the present invention there is further provided electrophoresis separation apparatus including a separation channel and disposed within the separation channel a separation medium. The separation medium includes polyacrylamide and dioxane and preferentially further includes one or more biopolymer denaturants and an ionic buffer.

The present invention further includes methods for electrophoretically separating analytes by introducing analytes into a separation channel of the present invention, applying an electric field across the separation channel and allowing the analytes to electrokinetically migrate within the separation medium. Preferred embodiments of this aspect include the electrophoretic separation of DNA fragments obtained using standard DNA sequencing chemistries.

This invention includes the use of 1,3-dioxane, 1,4-dioxane, as well as mixtures of the isomers.

An apparatus suitable for use of the electrophoresis gel of the present invention is shown in the FIGURE. The apparatus comprises a gel syringe 12 for introducing a sample through a valve 14 into a capillary 16. The distal end of the capillary is provided with a window 18 for incoming laser light for detection. The laser light is provided by laser light source 20, with the laser light going through a filter 22 and a focusing lens 24, and into the window through a parabolic light shield 26. Light emitted from the capillary passes through emission filters 30 into a photomultiplier 32, and signals from the photomultiplier 32 are collected by data acquisition means 34. A power supply 42 provides the electrical charge across the capillary. Spent sample and gel are withdrawn from the capillary through a valve 50.

The following Examples are illustrative.

EXAMPLE 1

Procedure For The Preparation Of Gel

The materials listed here are for the preparation of 150 mL. of 3T gel containing 15% dioxane, 100 mM Tris-Borate EDTA and 3.5 M urea.

| | |
|---|---|
| Acrylamide(Ultra Pure) | 4.5 g |
| Urea(Ultra Pure) | 10.5 g |
| 1,4 Dioxane | 7.5 mL. |
| Tris (Tris[hydroxymethyl] amino-methane] borate)(Ultra Pure) | 30.25 g |
| Boric Acid | 15.46 g |
| EDTA-(Ethylenediamine Tetraacetic acid) | 14.61 g |
| Resin* (AG 501-XA 20–50 mesh) | 1.5 g |
| APS(Ammonium Persulfate) | 0.1 g |
| TEMED(N,N,N$^1$,N$^1$-Tetramethylenediamine) | 100 uL |
| Shaker and/or Roller | |

*The Resin is sold by Bio Rad Laboratories under the designation 142–6425. The resin serves to remove unwanted ions from the buffer and the gel solution.

Buffer and Preparation

A. TRIS-BORATE-EDTA (500 mL):
  a) Prepare 0.5 M EDTA stock solution by dissolving 14.61 g of EDTA in 100 mL (total volume after adjusting the pH) of deionized water.
  b) Adjust the pH to 8.0 with concentrated NaOH.
  c) Prepare Tris-Borate EDTA solution by dissolving 30.25 g of Tris, 15.46 g of Boric Acid and 5 mL of 0.5 M EDTA (from step b) in water to a total volume of 500 mL. Filter through 0.2 micron filter. This solution is stable at room temperature for 60 days.

B. Gel (50 ml):
  a) Dissolve, very slowly, 10.5 g of urea and 7.5 mL of 1,4 dioxane in deionized water to a final volume of 40 mL. Wait until completely dissolved.
  b) Add 4.5 g of acrylamide to the solution and dissolve completely.
  c) Add 1.5 g of resin and stir for 15 minutes. Filter the solution through 0.2 micron filter to remove the Resin which is discarded.

d) Transfer the solution to a 60 mL serum bottle.

e) Add 10 mL of the Tris-Borate-EDTA solution from step A(c) to the bottle and mix. Cap and seal the bottle.

f) Purge the solution with Helium for 1 hour.

g) Pressurize the bottle with Argon at 20 psi for 30 seconds.

h) Remove the bottle and keep in ice for 15–20 minutes. To prevent partial polymerization of the gel, cool all sides of the bottle uniformly.

C. Gel Polymerization:

The following steps preferably are completed in less than five minutes for proper polymerization.

a) Dissolve 100 uL of TEMED in 900 uL of deionized water and keep on ice.

b) Dissolve 0.1 g of APS in 1.0 mL of deionized water and keep on ice.

c) Add 25 uL of each TEMED and APS solution to the bottle containing the acrylamide solution from step B(h).

d) Mix the solution and keep at 2–8° C. (with no disturbance) for 20–24 hrs.

D. Gel Preparation:

a) Prepare 100 mL of 100 mM Tris-Borate-EDTA, 15% dioxane and 3.5 M Urea buffer by dissolving 21.0 g of Urea, 15 mL of 1,4 Dioxane and 20.0 mL of Tris-Borate-EDTA in deionized water to a final volume of 100 mL. Filter the solution through 0.2 micron filter.

b) Transfer the buffer to a 250 mL glass bottle.

c) Add the polymerized gel from step C(d) to the bottle.

d) Purge the solution with pure oxygen for 15 minutes.

e) Cap the bottle and shake for 24–30 hrs at room temperature. f) Remove the bottle from shaker and keep at 2–8 C.

E. Gel Composition:

The electrophoresis separation gel resulting from step D has the following composition:

Polyacrylamide=3.0 grams/100 mL (total gel volume)

Dioxane (15%)=15 mL/100 mL (total gel volume)

Urea (3.5 Molar)=21.02 grams/100 mL (total gel volume)

Tris (100 millimolar)—1.21 grams/100 mL (total gel volume)

Boric Acid (100 millimolar)—0.62 gram/100 mL (total gel volume)

TEMED (0.0017%)=0.0017 mL/100 mL (total gel volume)

APS (0.0017%)=0.0017 gram/100 mL (total gel volume)

EDTA (1.0 millimolar)=0.292 gram/100 mL (total gel volume)

Water is used to dissolve the materials to reach final volume of 100 mL gel solution.

EXAMPLE 2

A first electrophoretic gel which contained 1,4 dioxane was prepared according to Example 1 and had the composition set forth in Step E.

A second gel was prepared which was identical to the first gel except that the 1,4-dioxane was omitted.

Each of the gels was incorporated in a standard electrophoresis capillary utilizing the equipment of FIG. 1. Electrophoresis was carried out on a sequencer provided with a laser equipped with an optical system which causes the beam to impinge on the capillary. The light reflected by the capillary is sensed by a detector and the detector output is computer processed to generate a tracing. An array of DNA fragments containing over 500 base pairs was used as the analytes to be separated. The mixture of DNA fragments was prepared for sequencing by conventional cleavage techniques. The same DNA fragments were used with both gels.

The sequencing labeling chemistries were a single dye reaction performed on a M13 mp18 DNA template and terminated with dideoxythymidine triphosphate. The product was purified by ethanol precipitation. Prior to injection the sample was heated to 95° C. for 2 minutes and then cooled to room temperature.

A manual hand operated pressure pump was used to introduce the polymer into the capillary (45 cm long) in less than one minute. The sieving matrix was used as the run buffer for each electrode (cathode and anode). After the filling process was complete, a 5 minute pre-run electrophoresis was done at 10–15 kilovolts (kV) prior to sample injection to monitor the current. Electrophoresis (at 10 kV) was continued after sample injection which was introduced by electrokinetic injection at 10 kV for 3–5 seconds. The electrophoresis voltage was supplied by a 15 kV power supply and runs were performed at 30° C. Capillary sieving buffer was contained in 4 mL glass vials placed in a vial holder inside the CE breadboard device.

The equipment used was a basic single capillary electrophoresis system with laser excitation source. The light from a laser source was passed through a filter to isolate the desired wavelength. The laser emission was then reflected by a mirror positioned at 90° relative to the lens. The lens was used to focus the laser light into the capillary. The capillary (100 micron i.d. and 735 micron o.d.) was maintained horizontal. Detection was accomplished with a photomultiplier tube. Full spectral data were acquired.

Both gels were effective in detecting the separation in the range up to about 480 base pairs. However, without dioxane, the peaks in an electrophoretic tracing are not clearly resolved at peaks 485 to 487, 505 & 506. The gel containing the dioxanes clearly resolved these peaks reflecting improved resolution.

These results demonstrate that the present invention provides a higher detection limit which permits the detection of a greater number of DNA fragments in a single separation, thereby facilitating more rapid analysis and sequencing of fragments.

These and other aspects and advantages associated with the present invention will become apparent to those skilled in the art upon an understanding of the invention as described in the detailed description of the invention taken in combination with the enclosed drawing.

What is claimed is:

1. An electrophoresis gel separation medium comprising polyacrylamide and a dioxane, wherein the polyacrylamide is present in about 1 to about 5 grams and the dioxane is present in an amount of from about 5 to 30 ml based upon 100 ml of said gel.

2. The separation medium of claim 1 wherein the gel includes water.

3. The separation medium of claim 1 wherein the polyacrylamide is present in about 3 grams and the dioxane is present in an amount of about 15 ml, based on 100 ml of said gel.

4. The separation medium of claim 1 wherein the polyacrylamide is a linear polymer.

5. The separation medium of claim 1 further including urea.

6. The separation medium of claim 1 wherein dioxane is 1,4-dioxane.

7. A electrophoresis separation system comprising: a separation channel, said separation channel including a separation medium comprising polyacrylamide and a dioxane wherein the polyacrylamide is present in about 1 to about 5 grams and the dioxane is present in an amount from about 5 to about 30 ml, based upon 100 ml of gel.

8. The electrophoresis separation system of claim 7 wherein said separation channel is a capillary tube.

9. The electrophoresis separation system of claim 7 wherein said separation channel is a planar capillary electrophoresis channel.

10. The electrophoresis separation system of claim 7 wherein the gel includes water.

11. The electrophoresis separation system of claim 7 wherein the polyacrylamide is present in about 3 grams and the dioxane is present in an amount of about 15 ml, based on 100 ml of said gel.

12. The electrophoresis separation system of claim 7 wherein the polyacrylamide is a linear polymer.

13. The electrophoresis separation system of claim 7 further including urea.

14. The electrophoresis separation system of claim 7 wherein dioxane is 1,4-dioxane.

15. In a method for electrophoretically separating analytes by introducing analytes into a separation channel containing separation media, applying an electric field across the separation channel and allowing the analytes to electrokinetically migrate within the separation medium, the improvement wherein the separation channel comprises an electrophoresis separation medium comprising polyacrylamide and a dioxane wherein the polyacrylamide is present in about 1 to about 5 grams and the dioxane is present in an amount from about 5 to about 30 ml. based on 100 ml of said gel.

16. The method of claim 15 wherein the analytes are DNA fragments obtained using DNA sequencing chemistries.

17. The method of claim 15 wherein the gel includes water.

18. The method of claim 15 wherein the polyacrylamide is present in about 3 grams and the dioxane is present in an amount of about 15 ml, based on 100 ml of said gel.

19. The method of claim 15 wherein the polyacrylamide is a linear polymer.

20. The method of claim 15 further including urea.

21. The method of claim 15 wherein dioxane is 1,4-dioxane.

* * * * *